(12) United States Patent
Larson et al.

(10) Patent No.: US 7,284,401 B2
(45) Date of Patent: Oct. 23, 2007

(54) STENT REDUCING SYSTEM AND DEVICE

(75) Inventors: Karen Larson, Lino Lakes, MN (US); Karl A. Jagger, Deephaven, MN (US); Richard C. Gunderson, Maple Grove, MN (US); Michael Gerdts, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 685 days.

(21) Appl. No.: 10/755,752

(22) Filed: Jan. 12, 2004

(65) Prior Publication Data

US 2005/0154450 A1 Jul. 14, 2005

(51) Int. Cl.
*B21D 37/18* (2006.01)
*B21D 41/04* (2006.01)

(52) U.S. Cl. .................. 72/44; 72/54; 72/402

(58) Field of Classification Search ............. 72/402, 72/44–46, 463, 57, 58, 54
See application file for complete search history.

(56) References Cited

U.S. PATENT DOCUMENTS

| | | | |
|---|---|---|---|
| 5,138,864 A | 8/1992 | Tarpill | 74/409.12 |
| 5,893,852 A | 4/1999 | Morales | 606/108 |
| 5,893,867 A | 4/1999 | Bagaoisan et al. | 606/198 |
| 5,911,752 A | 6/1999 | Dustrude et al. | 623/1.1 |
| 5,972,016 A | 10/1999 | Morales | 606/198 |
| 5,992,000 A | 11/1999 | Humphrey et al. | 29/516 |
| 6,009,614 A | 1/2000 | Morales | 29/516 |
| 6,024,737 A | 2/2000 | Morales | 606/1 |
| 6,063,102 A | 5/2000 | Morales | 606/198 |
| 6,074,381 A | 6/2000 | Dinh et al. | 606/1 |
| 6,082,990 A | 7/2000 | Jackson et al. | 425/517 |
| 6,092,273 A | 7/2000 | Villareal | 29/516 |
| 6,108,886 A | 8/2000 | Kimes et al. | 29/280 |
| 6,123,712 A | 9/2000 | Di Caprio et al. | 606/108 |
| 6,141,855 A | 11/2000 | Morales | 29/516 |
| 6,167,605 B1 | 1/2001 | Morales | 29/282 |
| 6,168,921 B1 | 1/2001 | Riss et al. | 435/6 |
| 6,352,547 B1 | 3/2002 | Brown et al. | 606/198 |

(Continued)

FOREIGN PATENT DOCUMENTS

WO 2004/019768 3/2004

OTHER PUBLICATIONS

U.S. Appl. No. 09/404,986, filed Sep. 22, 1999, Leo Klisch; Larry Ulanowski; Justin Plessal; Lou Ellis; Andy Dusbabek; Linda Lorentzen; Scott Hanson; Chris Larson; Terry Brown.

*Primary Examiner*—Daniel C Crane
(74) *Attorney, Agent, or Firm*—Vidas, Arrett, Steinkraus

(57) ABSTRACT

A system for reducing the diameter of a stent comprises a stent contracting assembly and a fluid source. The assembly comprises a plurality of contracting members that define a diameter reduction chamber for receiving a stent. When the chamber is in a pre-reduction configuration the stent has a first diameter and when the chamber is in a reduced configuration the stent has a second diameter. The second diameter is less than the first diameter. The fluid source is in fluid communication with the chamber and is constructed and arranged to inject a fluid therein. The fluid forms a fluid bearing between the contracting members and the stent which prevents the contracting members from contacting the stent in the reduced diameter configuration.

33 Claims, 12 Drawing Sheets

U.S. PATENT DOCUMENTS

| | | | |
|---|---|---|---|
| 6,360,577 B2 | 3/2002 | Austin | 74/402 |
| 6,364,870 B1 | 4/2002 | Pinchasik | 606/1 |
| 6,387,117 B1 | 5/2002 | Arnold, Jr. et al. | 623/1.1 |
| 6,387,118 B1 | 5/2002 | Hanson | 623/1.11 |
| 6,510,722 B1 | 1/2003 | Ching et al. | 72/402 |
| 6,568,235 B1 | 5/2003 | Kokish | 72/402 |
| 6,629,350 B2 | 10/2003 | Motsenbocker | 29/283.5 |
| 6,640,412 B2 | 11/2003 | Iancea | 29/505 |
| 6,666,880 B1 | 12/2003 | Chiu et al. | 623/1.11 |
| 6,689,123 B2 | 2/2004 | Pinchasik | 606/1 |
| 6,925,847 B2 * | 8/2005 | Motsenbocker | 72/402 |
| 2003/0056360 A1 | 3/2003 | Brown | 29/516 |
| 2003/0192164 A1 | 10/2003 | Austin | 29/505 |
| 2004/0093720 A1 | 5/2004 | Motsenbocker | 29/700 |
| 2004/0181236 A1 * | 9/2004 | Eidenschink et al. | 606/108 |

\* cited by examiner

STENT REDUCING SYSTEM AND DEVICE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to stents, stent loading, stent contracting and stent delivery systems and their respective methods of use. Some embodiments of the invention are more specifically directed to stent loading and crimping systems which are configured for reduced frictional interface between a stent and one or more system component which contact the stent during the crimping and loading process.

2. Description of Related Art

A stent is a generally tubular device that is used to support a bodily lumen. A stent is typically delivered to a desired bodily location via a catheter. Often the stent is loaded onto a portion of the catheter, such as a balloon or other region of the catheter shaft. In some stent delivery systems the stent is crimped to the catheter in order to minimize the profile of the stent on the catheter and to prevent undesired movement of the stent relative to the catheter shaft.

A number of techniques for loading and contracting a stent to a catheter shaft or balloon are used. One such technique that is commonly used in the radiological suite involves hand crimping the stent to the balloon. A stent is placed over an uninflated balloon and then squeezed with the fingers until the stent is in intimate contact with the uninflated balloon. The technique is highly operator dependent and can affect stent profile and stent placement with respect to the balloon and radiopaque markers. It can also affect the dilatation length of the stent and lead to pinching of the balloon.

Other techniques for crimping stents involve the use of mechanical devices for crimping stents. Mechanical stent crimpers have been disclosed in a number of patents including U.S. Pat. Nos. 6,387,118; U.S. Pat. No. 6,360,577; U.S. Pat. No. 6,108,886; U.S. Pat. No. 6,092,273 U.S. Pat. No. 6,082,990; U.S. Pat. No. 6,074,381; U.S. Pat. No. 6,063,102 and U.S. Pat. No. 5,992,000. Mechanical stent have also been disclosed in a number of copending, commonly assigned patent applications including U.S. application Ser. Nos. 09/401467, 09/401213, and 09/404986.

In many current stent loading operations particularly those involving self-expanding nitinol or shape memory stents the stent is dipped or sprayed with liquid nitrogen or other cooling agent in order for the stent to achieve a martensitic state. While in the martensitic state the stent is constrained via a crimper or other reducing device. In some cases the crimper comprises an adjustable stent diameter reducing chamber or opening through which the stent is advanced in order to uniformly reduce or compress the stent about its circumference.

Stent crimpers may have a variety of configurations and mechanisms for providing the stent diameter reduction chamber. For example, an iris type chamber wherein a plurality of members or blades are moved relative to the stent to reduce or expand the diameter of the chamber is described in U.S. Pat. No. 6,360,577, a crimper having a chamber defined by a plurality of member which extend inward to contract the chamber in a "star" or other geometric configuration is described in U.S. Pat. No. 6,168,921, a crimper having a pair of jaws or members that are moved relative to one another to reduce or expand the diameter of the chamber is described in U.S. Pat. No. 6,387,117, and a crimper having one or more conical apertures which at least partially define the chamber is described in U.S. Pat. No. 5,992,000. Crimpers having other configurations are also known. The entire content of each of the references cited above are incorporated herein by reference.

In many crimper assemblies a mandrel or push rod is utilized to drive the stent through the closed iris into a stent delivery mechanism such as a catheter.

In many crimper designs however, the crimping members or blades will come into direct contact with the stent being crimped as the iris is closed radially inward about the stent. After the stent has been reduced in diameter, in many instances the blades are kept in direct contact with the stent in order to keep the stent in the reduced state prior to loading of the stent onto a catheter or other delivery system. The stent is then transferred from the iris onto the delivery system by advancing a push rod or mandrel through the closed iris. In order to expel the stent from the iris the longitudinal force exerted on the stent by the mandrel must be sufficient to disengage the stent from its contact with the blades. If the force exerted on the stent by the mandrel is greater than the column strength of the stent the stent will buckle thereby leading to an unsuccessful loading of the stent. Unfortunately, such excessive force is often required to remove the stent from the crimper.

In addition to potentially buckling the stent, the force exerted by direct contact of the crimper blades on the stent as well as the act of pushing the stent out of the iris may have significant impact on any coating the stent may have even if the force is not excessive. For example where the stent includes one or more therapeutic coatings (i.e. a drug coated stent), direct contact of the stent by the blades during reduction, and/or the frictional interface of the blades and the stent during expulsion of the stent from the iris, may result in impairment of the coating thus reducing or negating its effectiveness.

In light of the above there is a need to provide stent reducing/loading systems with the capability to reduce and expel a stent, especially those stents having a therapeutic coating, from the reducing mechanism with reduced force and preferably with reduced contact between the stent and the reducing mechanism and/or push rod or support mandrel.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is particularly concerned with the crimping and otherwise reducing in size of stents, including bare or coated stents of any configuration or expansion type, including inflation expandable stents, self-expanding stents, hybrid expandable stents, etc. For the purpose of this disclosure, it is understood that the term 'stent' includes stents, stent-grafts, grafts and vena cava filters and other implantable medical devices for luminal support. It is also understood that the term 'crimping' refers to a reduction in size or profile of a stent and 'crimper' refers to devices for accomplishing such reduction in size or profile of a stent.

The present invention is embodied in a variety of forms. In at least one embodiment the invention is directed to a stent reducing and/or loading mechanisms such as stent crimpers and associated reducing and loading tools. In some embodiments a crimper comprises a contractible opening or stent reduction chamber defined by two or more members which define the opening. In at least one embodiment the chamber is an iris or other contractible and expandable opening defined by a plurality of moveable contacting members or blades. The chamber has a variable diameter and may be adjusted between an open diameter and a closed diameter. The crimper defines one or more spaces adjacent to each blade of the chamber. A fluid, such as a liquid or gas may be passed through one or more of theses spaces and into the chamber. The fluid forms a boundary layer between the blades and the stent to reduce friction between the blades and the stent. In some embodiments the presence of the fluid boundary layer minimizes adherence of the stent to the blades of the chamber.

In at least one embodiment the fluid forms a fluid bearing between the stent and the blades. The fluid bearing minimizes or eliminates direct contact between the stent and the crimping blades.

In at least one embodiment the fluid is cooled to a sufficiently low temperature so as to maintain a shape memory stent in a martensitic state, thereby inhibiting the stent composition form transitioning to an austenitic phase. In some embodiments the fluid is cooled to a predetermined temperature sufficient to provide the stent with a phase transformation from austenitic to martensitic.

In at least one embodiment an existing crimper is provided with a fluid source to inject fluid into the stent reduction chamber through the existing gaps between the blades. In some embodiments the blades of a crimper are modified to provide slots through which fluid may be channeled into the chamber.

In at least one embodiment the fluid is air.

In at least one embodiment the invention comprises a mandrel which supports the stent as it is advanced through the stent diameter reducing chamber. In some embodiments the mandrel has a stepped diameter which allows the stent to be secured at one or more of its proximal and distal ends by a raised diameter portion or collar of the mandrel. In some embodiments the distal end of the mandrel is tapered to facilitate alignment of the mandrel with a stent delivery system such as a catheter. In some embodiments the mandrel is provided with a polymer coating.

In at least one embodiment the mandrel defines a mandrel lumen. A fluid may be passed through the lumen to the stent and/or the chamber. In some embodiments the fluid passed through the lumen is liquid nitrogen, chilled air or a similar cooling composition.

In at least one embodiment the crimper defines a stepped diameter chamber. When the chamber is in the closed position about the stent a delivery system, such as a catheter, may be partially inserted into the larger diameter stepped region of the closed chamber in order to precisely align the stent and/or mandrel with the delivery system.

In at least one embodiment of the invention a vibratory mechanism is in communication with one or more components of a stent crimper and/or loading mandrel. The vibratory mechanism may apply vibratory energy to the crimper, loading mandrel, stent, and/or delivery system to aid in minimizing frictional interface therebetween. In some embodiments vibratory energy may also be selectively applied to the crimper following contraction of the stent to aid in releasing the stent from the blades. In some embodiments vibratory energy may also be selectively applied to the mandrel once the stent is properly positioned within the delivery system in order to aid in releasing the stent from the mandrel. In some embodiments the vibratory energy is delivered at an ultrasonic frequency.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

As is depicted in the various FIGS. 1-12, the present invention comprises embodiments which address the shortcomings described above.

As indicated above, the present invention is embodied in a variety of forms. In at least one embodiment, such as for example in the embodiment depicted in FIG. 1, the invention is directed to a radial stent reducing assembly or crimper 10. Crimper 10 may have any configuration of contacting members and/or any configuration of stent diameter reducing chamber, such as has been described above.

Figure 1:
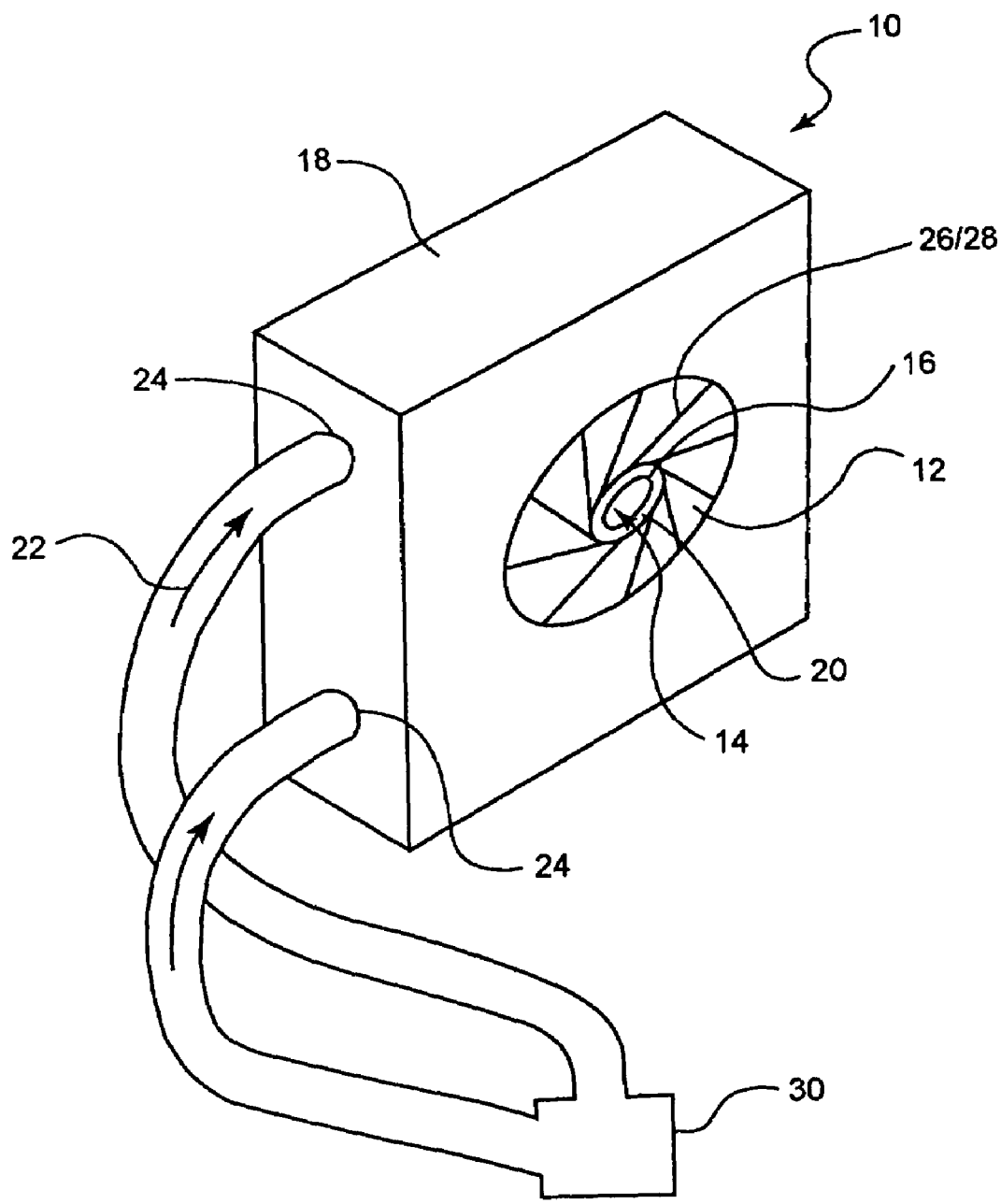
FIG. 1 is a perspective view of an embodiment of the invention wherein the stent reduction chamber is shown in the open or pre-reduction state.
Figure 2:
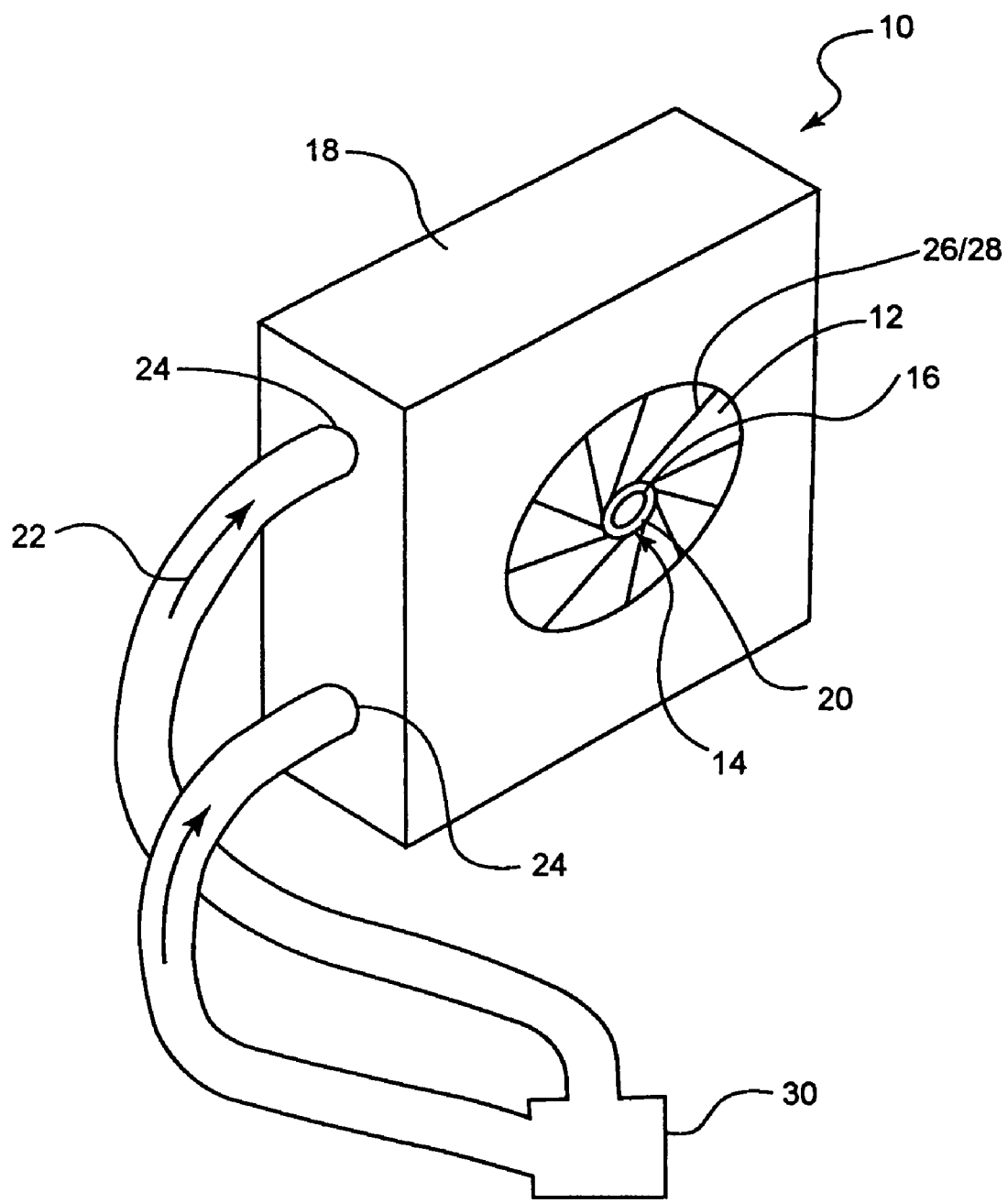
FIG. 2 is a perspective view of the embodiment shown in FIG. 1 wherein the chamber is shown in the closed or reduced state.
Figure 3:
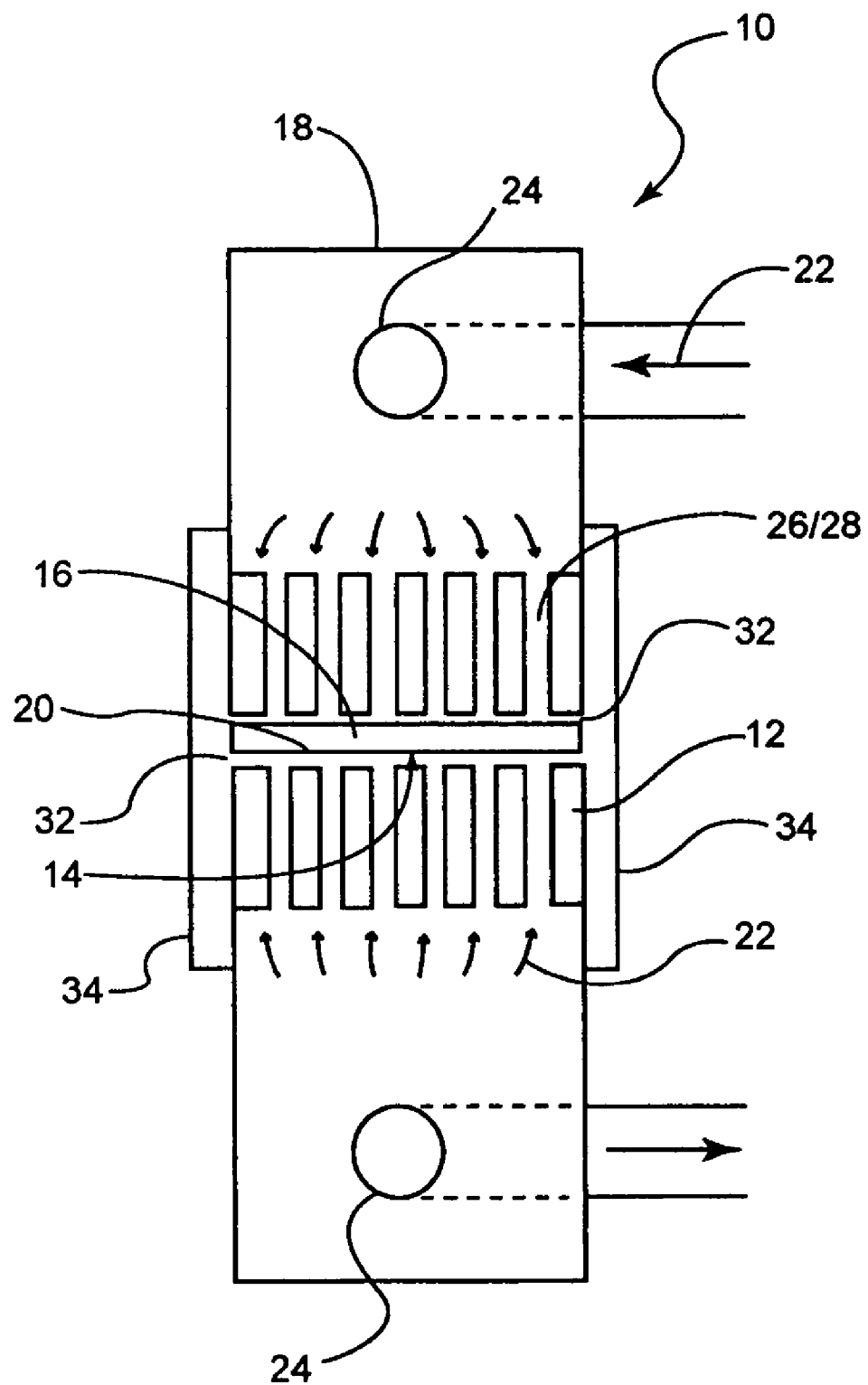
FIG. 3 is a partial cross-sectional side view of the embodiment shown in FIG. 2.

In the embodiment shown, crimper 10 is provided with a plurality of stent reducing members or blades 12 which define a stent reduction chamber 14 into which a stent or other medical device 16 is positioned in order to reduce the stent 16 from an unreduced diameter state, such as is shown in FIG. 1 to a reduced diameter state as is shown in FIG. 2. Unlike many prior stent crimping devices, the crimper 10 in the embodiment shown in FIGS. 1-3 is constructed and arranged to form a fluid bearing 20 between the blades 12 and the stent 16 during the crimping or reducing process. The fluid bearing 20 is formed by a fluid such as air, water, coolant, etc., indicated by arrows 22 in FIG. 3, which is injected into the chamber 14 through the blades 12 or through one or more passages therein and/or therebetween, such as is shown in FIG. 3. The presence of a fluid bearing 20 between the blades 12 and the stent 16 ensures that the stent 16 is not directly contacted by the blades 12 of the closing chamber 14 during the crimping process.

Blades 12 may be constructed from one or more metals, polymers or combinations thereof.

As is shown in FIGS. 1-2, the fluid bearing 20 is established by injecting fluid 22 from a fluid source 30 into the crimper housing 18 by one or more ports 24. Each port 24 is in fluid communication with the one or more fluid passages 26 between and/or within each blade 12. Each fluid passage 26 leads into the chamber 14. By injecting fluid into the chamber 14 under pressure, and substantially maintaining the fluid pressure within the chamber 14 during the crimping process, a fluid bearing 20 is formed between the blades 12 and the stent 16. In some embodiments fluid pressure is about 2 to about 20 psi.

In order to maintain the fluid pressure necessary to form the fluid bearing 20, the open ends 32 of the chamber 14 may be provided with one or more removable end seal members 34, such as is shown in FIG. 3. Seal members 34, be configured to include a variety of mechanisms. For example each member 34 may be configured as a simple fluid tight seal to prevent any fluid from escaping the chamber 14 during the crimping process. In some embodiments the members 34 may define a labyrinth passage which allows fluid 22 to escape the contracting chamber at a predetermined rate, in order to maintain a fluid bearing having a substantially constant pressure. In some embodiments the members 34 may define an opening therethrough which has a diameter less than that of the stent in the reduced state, in order to allow fluid 22 to pass from the chamber 14 which retaining the stent 16 therein. The members 34 may include one or more of the mechanisms described above as well as other mechanisms, such as adjustable valves, ports, seals, etc. for maintaining and/or regulating fluid pressure.

In some embodiments fluid 22 is injected into the housing 18 through one or more ports 24. In at least one embodiment, at least one port may be opened following the crimping process to allow the fluid 22 of the fluid bearing 20 to be purged from the chamber 14.

In some embodiments the fluid 22 is a fluid or combination of fluids including, but not limited to air, carbon dioxide, water, nitrous oxide, nitrogen gas or any other fluid for use in forming a fluid bearing 20 between two surfaces. In at least one embodiment fluid 22 is a bead-like substance that acts in the manner of a ball bearing. In some embodiments fluid 22 may remain on the stent surface post loading.

In some embodiment fluid 22 not only provides the fluid bearing 20, but where the fluid is cooled or is provided with a sufficiently low temperature, the fluid also acts to maintain a stent 16 constructed of a shape memory material, such as for example nitinol or other shape memory metals or polymers, in a martensitic state, thereby inhibiting the stent composition form transitioning to an austenitic phase. In some embodiments the fluid is cooled to a predetermined temperature sufficient to provide the stent with a phase transformation from austenitic state to martensitic state. In some embodiments the temperature is sufficient to reach the $M_f$ of Nitinol or other material from which the stent is constructed. In at least one embodiment the temperature of the fluid 22 is about −60° to about −80° Celsius. In an embodiment where the stent 16 is constructed of one or more polymers the fluid 22 has a temperature of just below the melting point of the polymer material.

Figure 4:
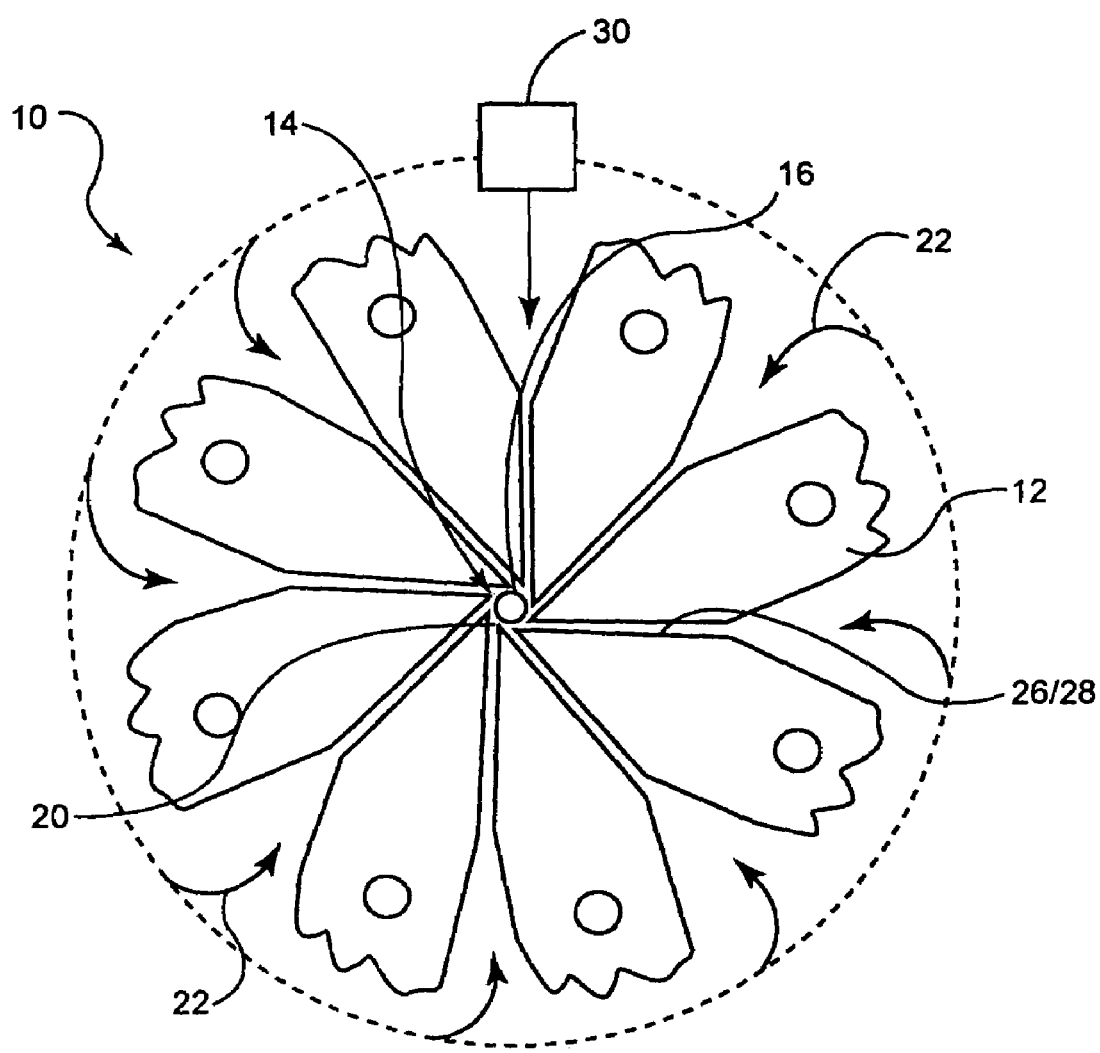
FIG. 4 is a partial close-up view of a portion of the embodiment shown in FIGS. 2 and 3.
Figure 5:
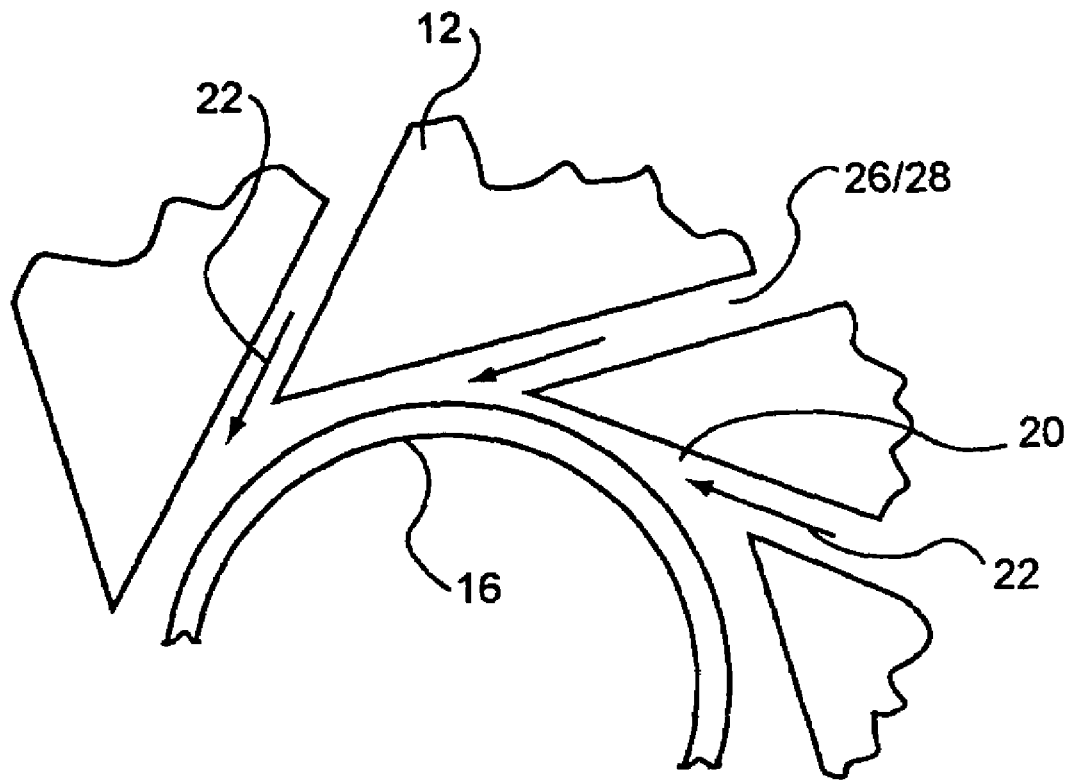
FIG. 5 is a partial close-up view of the embodiment depicted in FIG. 4 illustrating the fluid bearing between the stent and crimper.
Figure 6:
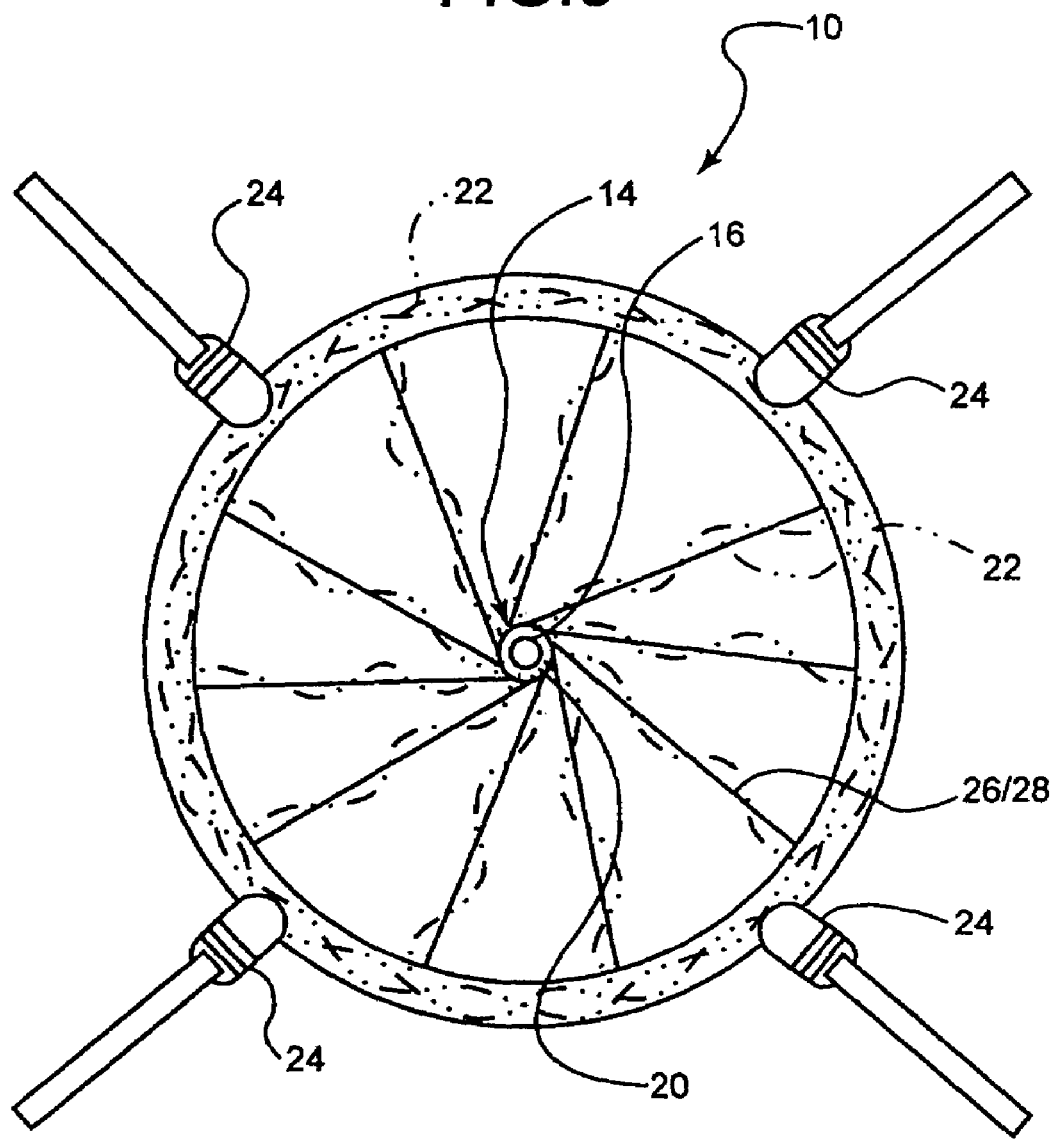
FIG. 6 is a partial cross-sectional end view of an iris configuration of the embodiment shown in FIGS. 2 and 3.

As indicated above, fluid 22 is injected into the chamber 14 through one or more fluid passages 26. In some embodiments, fluid passages 26 may be defined by the space 28 between longitudinally displaced blades 12 such as are shown n FIG. 3. In some embodiments the blades 12 are sized and shaped to define a space 28 radially between each blade 12 such as is shown in FIG. 4. When the blades 12 are contracted to reduce the chamber 14, such as is shown, the spaces 28 act as fluid passages 26 to transport fluid 22 into the chamber 14. In the configuration shown in FIG. 4, the fluid 22 form a fluid bearing 20 that effectively extends from the chamber 14 into the fluid passages 26, such as is best shown in FIG. 5. As a result, in this embodiment, wear resulting from contact between the blades is avoided as the fluid bearing 20 acts to not only prevent contact between the stent 16 and blades 12, but between the individual blades as well.

Figure 7:
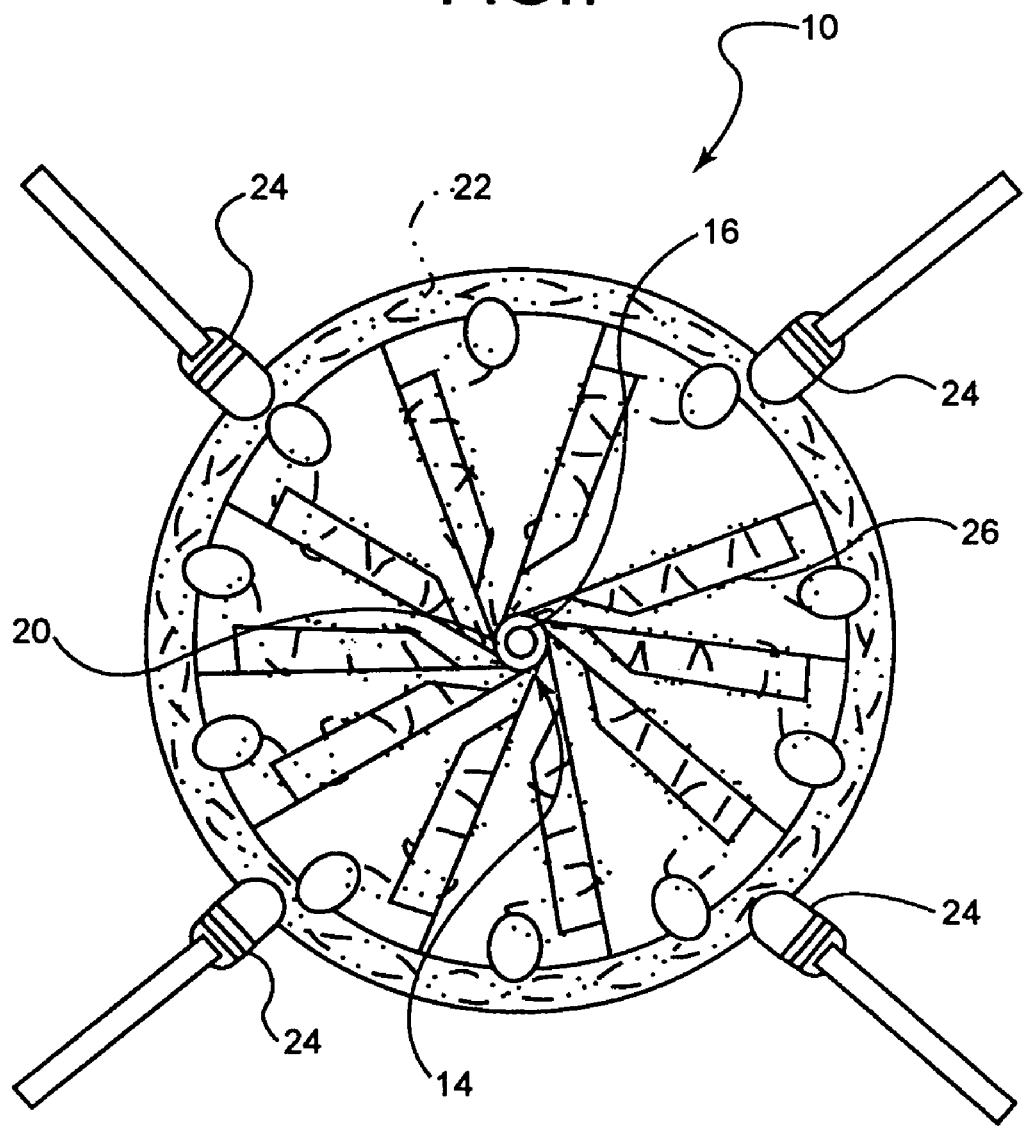
FIG. 7 is a partial cross-sectional end view of an iris configuration of the embodiment shown in FIGS. 2 and 3 wherein the crimping blades are provided with fluid passages.

As indicated above, the use of fluid 22 in forming a fluid bearing may be used in a variety of crimpers 10. In the embodiment shown in FIG. 6 for example, the crimper 10 is provided with an annular fluid passage 26 which is in fluid communication with four fluid ports 24. The fluid 22 is injected into the passage 26 and flows into the chamber 14 via the spaces 28 between the blades 12, which in some embodiments may be provided for as a result of the natural tolerances resulting from the blades' construction. In at least one embodiment, an example of which is shown in FIG. 7 one or more of the blades 12 is especially constructed to include fluid passages 26 between the adjacent blades 12.

Figure 8:
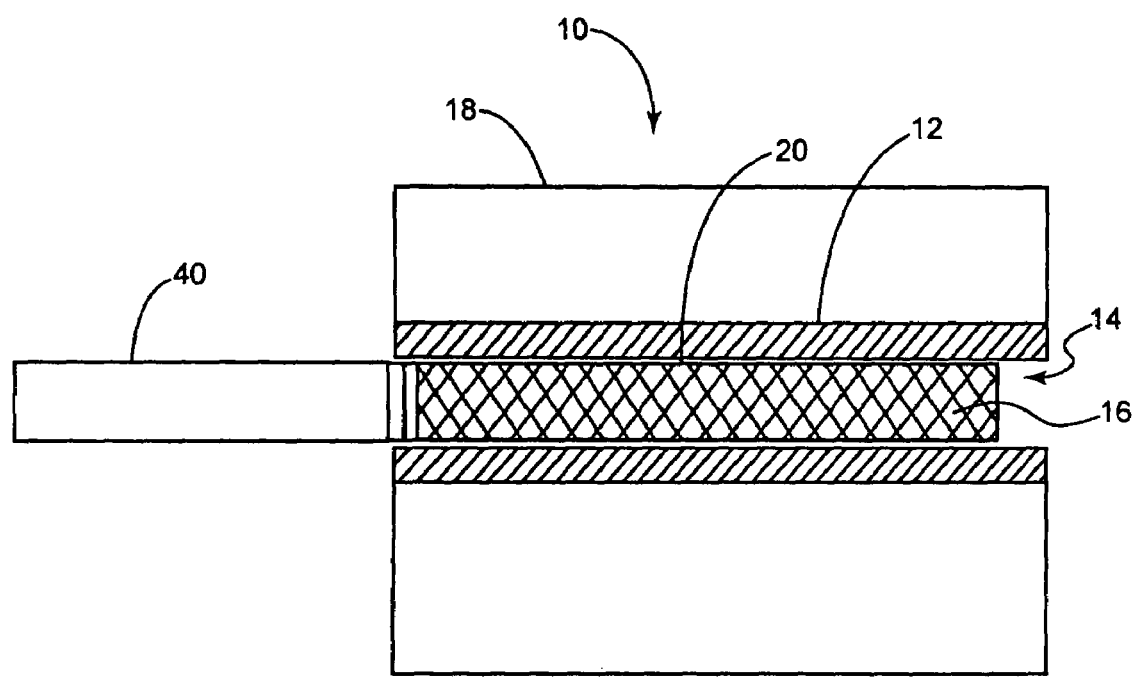
FIG. 8 is a partial close-up, cross-sectional side view of the embodiment shown in FIGS. 2 and 3 wherein the stent is shown being expelled from the crimper using a push rod or mandrel.

As is shown in FIG. 8, in some embodiments a push rod or mandrel 40 may be inserted into an end 32 of the chamber 14 during or subsequent to the reduction of the stent 16. The mandrel may supplement or replace one of the seal members in order to ensure that the formation and performance of the fluid bearing 20 is not compromised by the mandrel's use. In order to maximize the benefit of reducing contact between the blades 12 and the stent 16, in some embodiments the fluid bearing 20 is maintained even during expulsion of the stent 16 from the chamber 14 by advancing the mandrel 40 therethrough.

Figure 9:
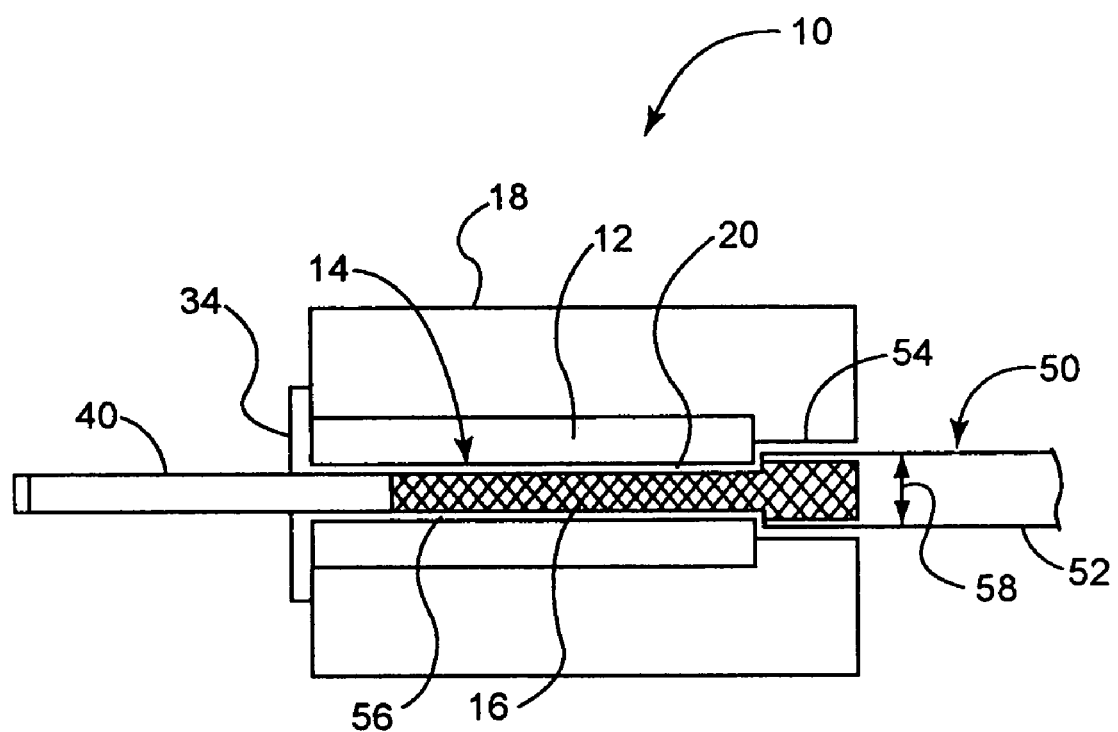
FIG. 9 is a partial close-up view of the embodiment depicted in FIG. 8 illustrating the loading of a stent into a stent delivery catheter wherein the crimper is provided with a stepped diameter reducing chamber.

As is shown in FIG. 9, in some embodiments, the reduced diameter stent 16 is loaded directly onto a catheter or other stent delivery system 50 by pushing the stent 16 through the chamber 14 and directly into the catheter's protective housing or sheath 52. In order to facilitate the loading of the reduced stent 16 onto the catheter 50, in some embodiments the crimper 10 may have a chamber 14 with a stepped diameter, to allow the catheter 50 to be partially inserted within the chamber 14.

The catheter receiving region 54 of the stepped diameter chamber 14 has a greater diameter than the stent reducing region 56. In at least one embodiment the inner diameter 58 of the catheter 50 is at least as large as the diameter of the stent reducing region 56 of the chamber 14. When a catheter 50 is engaged to the crimper 10 in the manner shown in FIG. 9, the stent 16 may be advanced directly into the sheath 52, without compromising the fluid bearing 20. Once the stent is loaded onto the catheter 50 the fluid bearing may be maintained within the catheter 50, or the fluid may be withdrawn from the catheter 50 by application of a vacuum or other mechanism.

Figure 10:
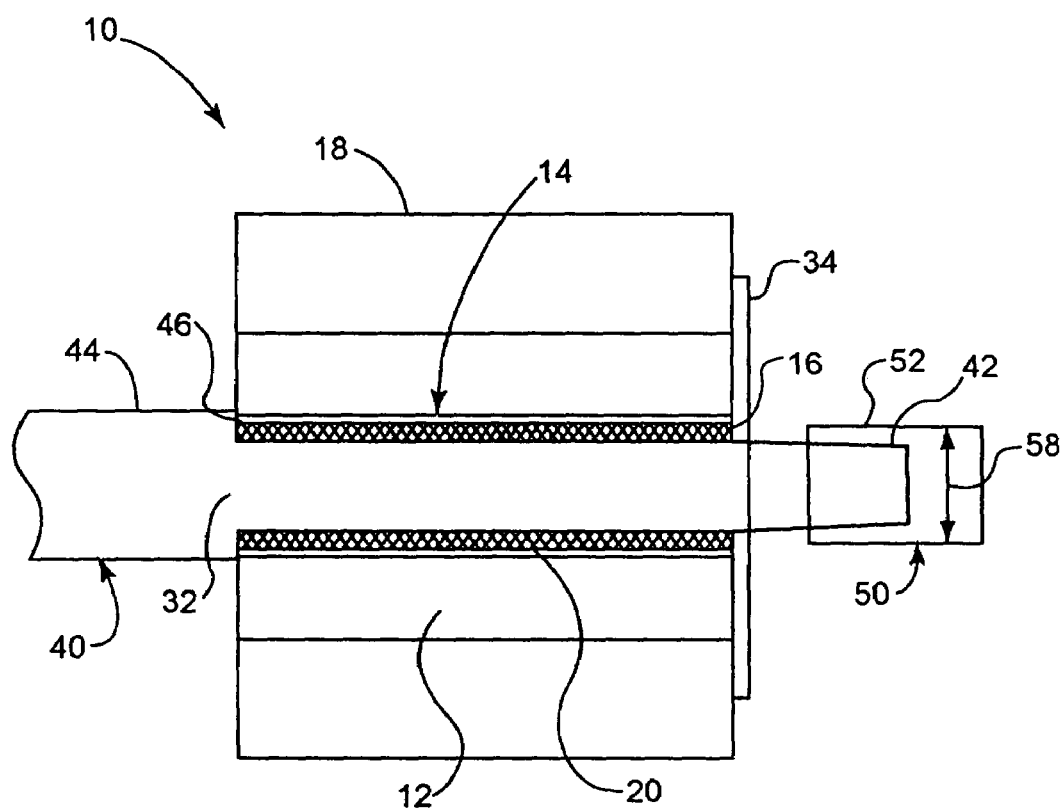
FIG. 10 is a partial cross-sectional side view of the embodiment shown in FIG. 8 wherein the stent is mounted on a configuration of the mandrel during the crimping process.
Figure 11:
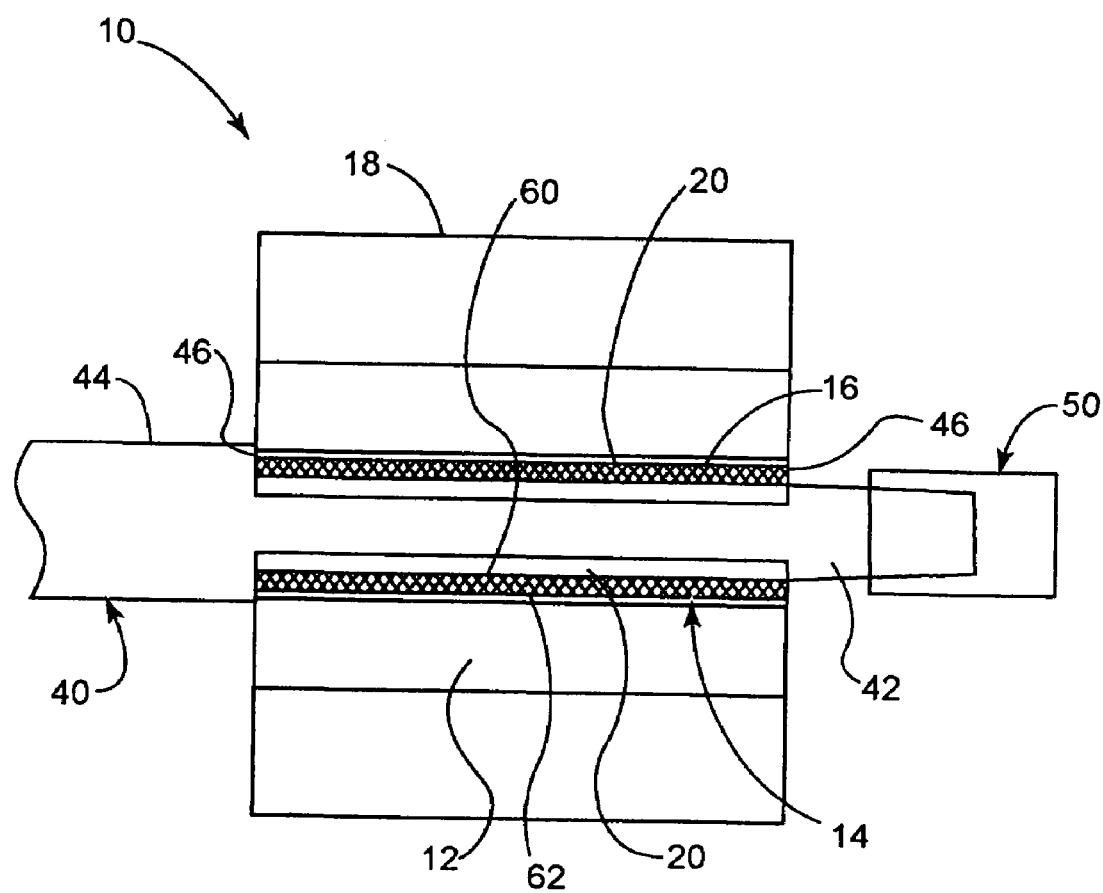
FIG. 11 is a partial cross-sectional side view of the embodiment shown in FIG. 8 wherein the stent is mounted on a configuration of the mandrel during the crimping process.
Figure 12:
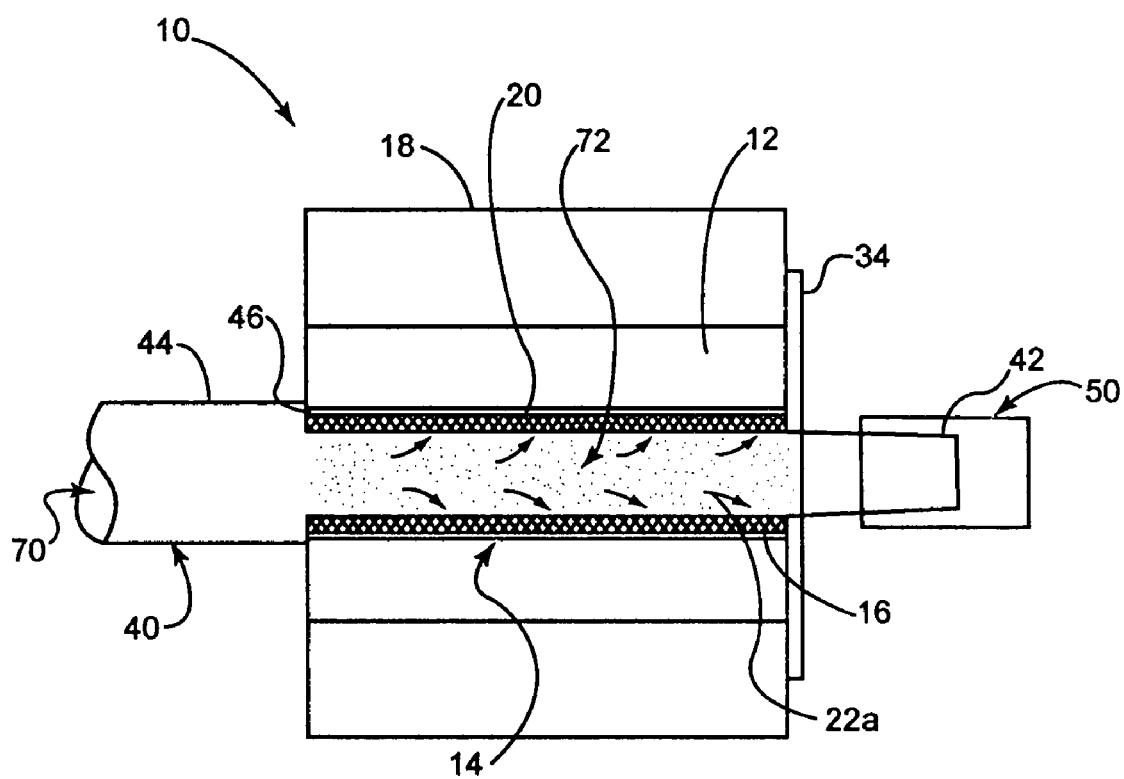
FIG. 12 is a partial cross-sectional side view of the embodiment shown in FIG. 8 wherein the stent is mounted on a configuration of the mandrel during the crimping process.

In some embodiments, some examples of which are depicted in FIGS. 10-12, the stent 16 is reduced within the crimper 10 while mounted on a portion of the mandrel 40. In the embodiment shown in FIG. 10, the mandrel 40 has a tapered distal end portion 42 which has a diameter less than that of the inner diameter 58 of a catheter 50. As a result, the mandrel 40, including the reduced diameter stent 16 may be readily advanced into the catheter 50 with minimal or no contact between the stent 16 and the sheath 52. In some embodiments the mandrel 40 further comprises a proximal end portion 44 which defines an annular seal 46, the annular seal 46 has a diameter larger than that of the chamber 14 in the closed or reduced configuration. As a result, the annular seal 46 may supplement or replace the need for a fluid seal member 34 at one end 32 of the chamber 14.

In the embodiment shown in FIG. 11, both the proximal end portion 44 and the distal end portion 42 of the mandrel 40 each comprise an annular seal 46. Each annular seal 46 acts as a fluid seal member, as described above. In at least one embodiment, the fluid bearing 20 forms not only between the blades 12 and the stent 16, but also between the portion of the mandrel 40 about which the stent 16 is disposed and the stent 16. Such a dual layer fluid bearing 20 protects both the inside surface 60 and outside surface 62 of the stent 16 from extraneous contact.

In at least one embodiment, such as is shown in FIG. 12, the mandrel 40 may define a fluid injection lumen 70 into which a fluid 22a may be injected. Mandrel 40 may further define one or more perfusion ports, openings, perforations or pores 72 through which the fluid 22a may pass from the lumen 70 and into the chamber 14. Fluid 22a injected into the chamber in this manner may be used to assist in forming the fluid bearing 20, and particularly a dual layer fluid bearing such as previously discussed. In some embodiments the fluid 22a passively, by cooling the mandrel 40, or actively, by directly flowing onto the stent 16, cools the stent 16 to a temperature sufficient to provide the stent with a phase transformation from austenitic to martensitic.

In such an embodiment the fluid 22a is cooled air, liquid nitrogen (nitrous oxide) or another suitable coolant.

In some embodiments, one or more blades 12, the mandrel 40 and/or the fluid 22 and/or 22a by be imparted with an ultrasonic or other form of vibratory energy in order to further facilitate minimization of the frictional interface between the stent 16 and the crimper 10 or any of its components.

In at least one embodiment the stent 16 as shown in any of the various FIGS. 1-12 may include one or more coatings and/or other delivery mechanisms which comprise one or more therapeutic agents, cellular materials, polymeric agents, drugs, etc.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vasoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$ $Lin^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$ $Lin^-CD34^+$—Presence of the cell surface protein CD34 has been used to identify hematopoietic stem cells. However, the marker is also present on progenitor cells and white blood cells of various levels of maturity.

$Lin^-cKit^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups.

Preferred polyolefinic blocks include polymeric blocks of isobutylene,

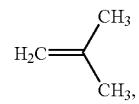

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

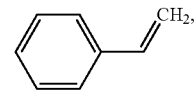

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X—(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

The inventive medical devices may also be provided with a sugar or more generally a carbohydrate and/or a gelatin to maintain the inventive medical devices on a balloon during delivery of the medical device to a desired bodily location. Other suitable compounds for treating the inventive medical devices include biodegradable polymers and polymers which are dissolvable in bodily fluids. Portions of the interior and/or exterior of the inventive medical devices may be coated or impregnated with the compound. Mechanical retention devices may also be used to maintain the inventive medical devices on the balloon during delivery.

The inventive medical devices may also be provided in whole or in part with one or more of the above therapeutic agents, polymeric coatings or the like. Where multiple therapeutic agents are provided, different coatings and/or mechanisms may release the drugs at different rates. For example, one therapeutic agent may be released at a fast rate and another therapeutic agent may be released at a slow rate. Where multiple polymeric coatings are provided, the coatings may degrade or erode at different rates.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A system for reducing the diameter of a stent comprising:
a stent contracting assembly, the stent contracting assembly comprising a plurality of moveable contracting members, the plurality of contracting members defining a diameter reduction chamber, the chamber having a reduced diameter configuration and a pre-reduction diameter configuration, the contracting assembly constructed and arranged to receive a stent into and through the chamber, wherein when the chamber is in the pre-reduction diameter configuration the stent has a first diameter and when the chamber is in the reduced diameter configuration the stent has a second diameter, the second diameter being less than the first diameter, wherein the chamber defines a first end opening and a second end opening, the stent being moveable through the chamber from the first end opening to the second end opening, the stent contracting assembly further comprising a housing, the plurality of moveable contracting members being mechanically engaged to the housing, the stent contracting assembly further comprising at least one seal member, the at least one seal member engaged to a portion of the housing adjacent to at least one of the first end opening and the second end opening of the chamber, the at least one seal member providing a fluid tight seal to the at least one of the first end opening and the second end opening;
a fluid source, the fluid source in fluid communication with the chamber, the fluid source constructed and arranged to provide a fluid bearing between the contracting members and the stent which prevents the contracting members from contacting the stent in the reduced diameter configuration;
wherein the stent contracting assembly defines at least one fluid injection port, the at least one fluid injection port in fluid communication with the chamber and the fluid source.

2. The system of claim 1 wherein the plurality of moveable contracting members are adjacent one another, adjacent contracting members defining a space therebetween, each space in fluid communication with the fluid source and the chamber.

3. The system of claim 2 wherein the plurality of moveable contracting members are positioned longitudinally adjacent one another.

4. The system of claim 2 wherein the plurality of moveable contracting members are positioned radially adjacent one another.

5. The system of claim 1 wherein at least one of the plurality of moveable contracting members defines a space the space in fluid communication with the fluid source and the chamber.

6. The system of claim 1, wherein in the reduced diameter configuration the diameter of the chamber in the first end region and the diameter of the chamber second end region are different.

7. The system of claim 6 wherein the diameter of the chamber in the second end region is greater than the diameter of the chamber in the first end region.

8. The system of claim 7 wherein the second end region is constructed and arranged to removably receive a portion of a catheter therein, the stent being loaded on to the catheter by advancing the stent through the chamber.

9. The system of claim 1, wherein at least one seal member comprises a first seal member and a second seal member, the first seal member engaged to a portion of the housing adjacent to the first end opening of the chamber and the second seal member engaged to a portion of the housing adjacent to the second end opening of the chamber.

10. The system of claim 1, wherein the at least one seal member comprises a removable fluid tight seal.

11. The system of claim 1, wherein the at least one seal member comprises a labyrinth.

12. The system of claim 1, wherein the at least one seal member comprises an adjustable valve.

13. The system of claim 1, further comprising a mandrel, in the reduced configuration the mandrel is constructed and arranged to be advanced through the chamber to expel the stent therefrom.

14. The system of claim1 13 wherein the mandrel has a diameter at least as great as that of the second diameter of the stent.

15. The system of claim 13 wherein the mandrel defines a stent mounting region, the stent being disposed about at least a portion of the stent mounting region.

16. The system of claim 15 wherein the mandrel further comprises a first end region and a second end region, the stent mounting region positioned between the first end region of the mandrel and the second end region of the mandrel, at least one of the first end region of the mandrel and the second end region of the mandrel having a diameter at least as great as the second diameter of the stent.

17. The system of claim 16 wherein the first end region of the mandrel is external and immediately adjacent to the first end opening of the chamber and the second end region of the mandrel is external and immediately adjacent to the second end opening of the chamber.

18. The system of claim 17 wherein the first end region of the mandrel is sealingly engaged to the first open end of the chamber.

19. The system of claim 17 wherein the second end region of the mandrel is sealingly engaged to the second open end of the chamber.

20. The system of claim 17 wherein the first end region of the mandrel is sealingly engaged to the first open end of the chamber and the second end region of the mandrel is sealingly engaged to the second open end of the chamber.

21. The system of claim 16 wherein at least a portion of the at least one of the first end region of the mandrel and the second end region of the mandrel are tapered.

22. The system of claim 15 wherein the mandrel defines a fluid injection lumen, a second fluid being injected into the fluid injection lumen.

23. The system of claim 22 wherein the second fluid is a coolant.

24. The system of claim 23 wherein the second fluid is substantially the same as the fluid from the fluid source.

25. The system of claim 22 wherein the at least a portion of the stent mounting region of the mandrel defines at least one perfusion port, the at least one perfusion port in fluid communication with the fluid injection lumen.

26. The system of claim 1 wherein the fluid is selected from a member of the group consisting of air, water, carbon dioxide, nitrous oxide, nitrogen gas and any combination thereof.

27. The system of claim 26 wherein the fluid is cooled to a temperature of about −60° Celsius to about −80° Celsius.

28. The system of claim 1 wherein at least a portion of the stent is coated with at least one therapeutic agent.

29. The system of claim 28 wherein the at least one therapeutic agent is at least one non-genetic therapeutic agent selected from at least one member of the group consisting of: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

30. The system of claim 28 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16, Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

31. The system of claim 28 wherein the at least one therapeutic agent is at least one type of cellular material selected from at least one member of the group consisting of: cells of human origin (autologous or allogeneic); cells of non-human origin (xenogeneic) and any combination thereof.

32. The system of claim 31 wherein the cellular material is selected from at least one member of the group consisting of: side population cells; lineage negative cells; lineage negative CD34⁻cells; lineage negative CD34⁺cells; lineage negative cKit⁺cells; mesenchymal stem cells; cord blood bells; cardiac or other tissue derived stem cells; whole bone marrow; bone marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts +5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; teratoma derived cells and any combinations thereof.

33. The system of claim 28 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof coatings from polymer dispersions such as polyurethane dispersions (BAYHDROL®, etc.), fibrin, collagen and derivatives thereof polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO₄'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; A block copolymers; B block copolymers and any combinations thereof.

* * * * *